(12) United States Patent
Ozaki et al.

(10) Patent No.: US 9,632,027 B2
(45) Date of Patent: Apr. 25, 2017

(54) SURFACE PLASMON RESONANCE SENSOR CELL AND SURFACE PLASMON RESONANCE SENSOR

(71) Applicant: NITTO DENKO CORPORATION, Ibaraki-shi, Osaka (JP)

(72) Inventors: Mayu Ozaki, Ibaraki (JP); Kazuto Yamagata, Ibaraki (JP); Naoki Nagaoka, Ibaraki (JP); Tomohiro Kontani, Ibaraki (JP)

(73) Assignee: NITTO DENKO CORPORATION, Ibaraki-shi (JP)

( * ) Notice: Subject to any disclaimer, the term of this patent is extended or adjusted under 35 U.S.C. 154(b) by 7 days.

(21) Appl. No.: 14/778,978

(22) PCT Filed: Feb. 26, 2014

(86) PCT No.: PCT/JP2014/054623
§ 371 (c)(1),
(2) Date: Sep. 21, 2015

(87) PCT Pub. No.: WO2014/148212
PCT Pub. Date: Sep. 25, 2014

(65) Prior Publication Data
US 2016/0047745 A1    Feb. 18, 2016

(30) Foreign Application Priority Data

Mar. 22, 2013 (JP) .................................. 2013-059813

(51) Int. Cl.
*G01N 21/55* (2014.01)
*G01N 21/552* (2014.01)
*G01N 21/77* (2006.01)

(52) U.S. Cl.
CPC ....... *G01N 21/553* (2013.01); *G01N 21/7703* (2013.01); *G01N 2021/7776* (2013.01); *G01N 2201/0638* (2013.01); *G01N 2201/08* (2013.01)

(58) Field of Classification Search
CPC .. G01N 21/553; G01N 21/7703; G01N 21/41; G01N 21/03
(Continued)

(56) References Cited

U.S. PATENT DOCUMENTS 5,327,225 A * 7/1994 Bender ................ G01N 21/553
                                                  250/307
5,359,681 A * 10/1994 Jorgenson ............ G01N 21/553
                                                  250/227.11
(Continued)

FOREIGN PATENT DOCUMENTS

CN    101038253 A    9/2007
CN    101936899 A    1/2011
(Continued)

OTHER PUBLICATIONS

ISA Japanese Patent Office, International Search Report Issued in Application No. PCT/JP2014/054623, May 20, 2014, WIPO, 2 pages.
(Continued)

*Primary Examiner* — Tarifur Chowdhury
*Assistant Examiner* — Isiaka Akanbi
(74) *Attorney, Agent, or Firm* — Alleman Hall McCoy Russell & Tuttle LLP

(57) ABSTRACT

The present invention provides an SPR sensor cell having very excellent detection sensitivity, the SPR sensor cell including: an under-cladding layer; a core layer formed so that at least a part of the core layer is adjacent to the under-cladding layer; and a metal layer covering the core
(Continued)

layer. In the SPR sensor cell, the core layer includes a uniform refractive index layer and a graded refractive index layer. The graded refractive index layer is arranged between the uniform refractive index layer and the metal layer. A refractive index of the graded refractive index layer is equal to or more than a refractive index of the uniform refractive index layer, and the refractive index of the graded refractive index layer increases continuously from a surface thereof on a uniform refractive index layer side to the metal layer side in a thickness direction of the graded refractive index layer.

6 Claims, 5 Drawing Sheets

(58) Field of Classification Search
USPC .................................................. 356/445–446
See application file for complete search history.

(56) References Cited

U.S. PATENT DOCUMENTS

| | | | | |
|---|---|---|---|---|
| 6,136,611 | A * | 10/2000 | Saaski | G01N 21/648 |
| | | | | 422/562 |
| 6,432,364 | B1 | 8/2002 | Negami et al. | |
| 9,285,534 | B2 * | 3/2016 | Lee | G02B 6/02 |
| 2005/0018949 | A1 * | 1/2005 | Yan | B82Y 20/00 |
| | | | | 385/14 |
| 2006/0109471 | A1 | 5/2006 | Lin et al. | |
| 2006/0193550 | A1 * | 8/2006 | Wawro | G01N 21/648 |
| | | | | 385/12 |
| 2009/0103099 | A1 * | 4/2009 | Debackere | B82Y 20/00 |
| | | | | 356/445 |
| 2015/0260649 | A1 * | 9/2015 | Nishio | G01N 21/553 |
| | | | | 385/12 |

FOREIGN PATENT DOCUMENTS

| | | |
|---|---|---|
| EP | 0971226 A1 | 1/2000 |
| JP | 200019100 A | 1/2000 |
| JP | 2008083036 A | 4/2008 |
| JP | 2010223817 A | 10/2010 |
| JP | 2012107902 A | 6/2012 |
| JP | 2012215541 A | 11/2012 |
| WO | 2008075578 A1 | 6/2008 |

OTHER PUBLICATIONS

Weiss, M. et al., "A theoretical investigation of environmental monitoring using surface plasmon resonance waveguid sensors," Sensors and Actuators A: Physical, vol. 51, No. 2-3, Nov. 1995, 7 pages.

Hosoki, A. et al., "A surface plasmon resonance hydrogen sensor using Au/Ta2O5/Pd multi-layers on hetero-core optical fiber structures," Sensors and Actuators B: Chemical, vol. 185, Aug. 2013, Published Online May 4, 2013, 6 pages.

State Intellectual Property Office of the People's Republic of China, Office Action and Search Report Issued in Application No. 201480017509.5, Nov. 4, 2016, 18 pages. (Submitted with Partial Translation).

European Patent Office, Extended European Search Report Issued in Application No. 14768005.2, Nov. 16, 2016, Germany, 8 pages.

* cited by examiner

SURFACE PLASMON RESONANCE SENSOR CELL AND SURFACE PLASMON RESONANCE SENSOR

TECHNICAL FIELD

The present invention relates to an SPR sensor cell and an SPR sensor. More specifically, the present invention relates to an SPR sensor cell including an optical waveguide and an SPR sensor.

BACKGROUND ART

Hitherto, in the fields of chemical analysis, biochemical analysis, and the like, a surface plasmon resonance (SPR) sensor including an optical fiber has been used. In the SPR sensor including an optical fiber, a metal thin-film is formed on an outer circumferential surface of a tip end portion of the optical fiber, and an analysis sample is fixed to the optical fiber into which light is guided. Of the light to be guided, light having a particular wavelength generates surface plasmon resonance in the metal thin-film, and light intensity thereof is attenuated. In such an SPR sensor, the wavelength of the light generating surface plasmon resonance generally varies depending on a refractive index of an analysis sample to be fixed to the optical fiber. Therefore, if a wavelength at which light intensity is attenuated after the generation of surface plasmon resonance is measured, the wavelength of the light generating surface plasmon resonance can be identified. Further, if a change in the wavelength at which light intensity is attenuated is detected, it can be confirmed that the wavelength of the light generating surface plasmon resonance has changed, and hence a change in the refractive index of the analysis sample can be confirmed. As a result, such an SPR sensor can be used for various chemical analyses and biochemical analyses such as measurement of a sample concentration and detection of an immunoreaction.

In the SPR sensor including an optical fiber, the tip end portion of the optical fiber has a fine cylindrical shape, and hence there is a problem in that it is difficult to form the metal thin-film and fix an analysis sample to the optical fiber. In order to solve the problem, for example, there has been proposed an SPR sensor cell including a core through which light is transmitted and a clad covering the core, in which a through-hole extending to a surface of the core is formed at a predetermined position of the clad, and a metal thin-film is formed on the surface of the core at a position corresponding to the through-hole (for example, Patent Literature 1). In such an SPR sensor cell, it is easy to form the metal thin-film for generating surface plasmon resonance on the surface of the core and fix the analysis sample onto the surface. Further, it has been proposed that the detection accuracy of the SPR sensor cell can be enhanced by continuously changing the refractive index of a region on an under-cladding layer side in the core layer in the SPR censor cell (Patent Literature 2).

However, in recent years, in chemical analysis and biochemical analysis, there is an increasing demand for detection of a minute change and/or a trace amount of component, and thus further enhancement of detection sensitivity of the SPR sensor cell is being demanded.

CITATION LIST

Patent Literature

[PTL 1] JP 2000-19100 A
[PTL 2] JP 2012-107902 A

SUMMARY OF INVENTION

Technical Problem

The present invention has been made in view of solving the conventional problem, and an object of the present invention is to provide an SPR sensor cell having very excellent detection sensitivity and an SPR sensor.

Solution to Problem

According to one embodiment of the present invention, there is provided an SPR sensor cell. The SPR sensor cell according to the one embodiment of the present invention includes: an under-cladding layer; a core layer formed so that at least a part of the core layer is adjacent to the under-cladding layer; and a metal layer covering the core layer, in which: the core layer includes a uniform refractive index layer and a graded refractive index layer; the graded refractive index layer is arranged between the uniform refractive index layer and the metal layer; and a refractive index of the graded refractive index layer is equal to or greater than a refractive index of the uniform refractive index layer, and the refractive index of the graded refractive index layer increases continuously from a surface thereof on a uniform refractive index layer side to a metal layer side in a thickness direction of the graded refractive index layer.

In a preferred embodiment of the present invention, the graded refractive index layer has a thickness from 1 µm to 30 µm.

In a preferred embodiment of the present invention, a change in refractive index of the graded refractive index layer ($\Delta N = N_{max} - N_{min}$: where $N_{max}$ represents a maximum refractive index of the graded refractive index layer, and $N_{min}$ represents a minimum refractive index of the graded refractive index layer) is from 0.001 to 0.035.

In a preferred embodiment of the present invention, a thickness (Tb (µm)) of the graded refractive index layer and a change in refractive index of the graded refractive index layer ($\Delta N = N_{max} - N_{min}$: where $N_{max}$ represents a maximum refractive index of the graded refractive index layer, and $N_{min}$ represents a minimum refractive index of the graded refractive index layer) satisfy a relationship of $0.5 \times 10^{-3} \leq \Delta N / Tb \leq 20.0 \times 10^{-3}$.

In a preferred embodiment of the present invention, a refractive index ($N_{CO}$) of the uniform refractive index layer satisfies a relationship of $1.34 \leq N_{CO} \leq 1.43$.

According to another aspect of the present invention, there is provided an SPR sensor. The SPR sensor includes the SPR sensor cell described above.

Advantageous Effects of Invention

According to the one embodiment of the present invention, the SPR sensor cell and the SPR sensor that are excellent in signal intensity may be provided by continuously increasing the refractive index of the core layer in the vicinity of an interface between the core layer and the metal layer toward the metal layer side.

DESCRIPTION OF EMBODIMENTS

A. SPR Sensor Cell

Figure 1:
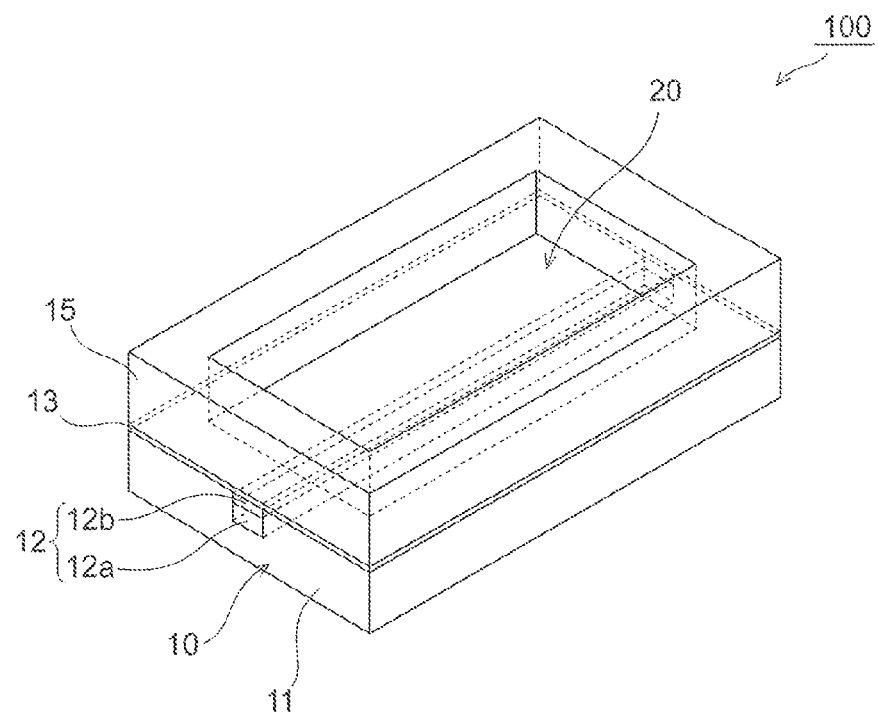
FIG. 1 is a schematic perspective view for illustrating an SPR sensor cell according to a preferred embodiment of the present invention.
Figure 2:
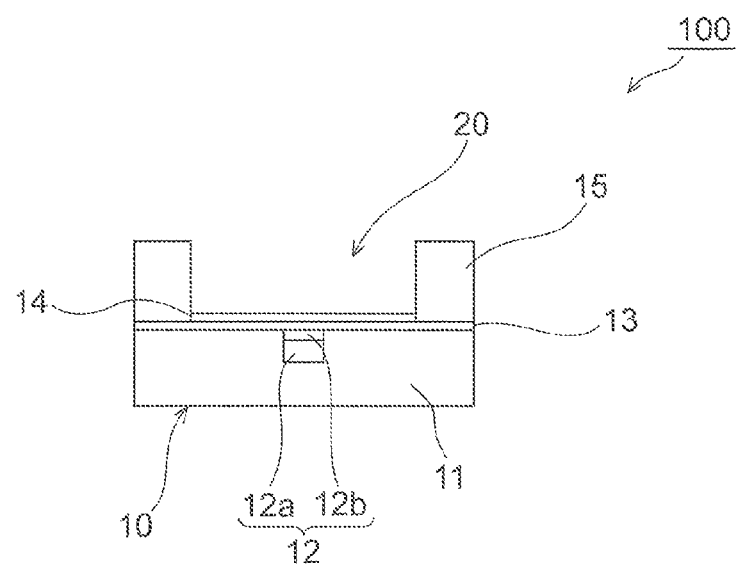
FIG. 2 is a schematic sectional view of the SPR sensor cell illustrated in FIG. 1.

FIG. 1 is a schematic perspective view for illustrating an SPR sensor cell according to a preferred embodiment of the present invention. FIG. 2 is a schematic sectional view of the SPR sensor cell illustrated in FIG. 1. It should be noted that, when a direction is mentioned in the following description of the SPR sensor cell, an upper side of the figure is defined as an upper side, and a lower side of the figure is defined as a lower side.

As illustrated in FIG. 1 and FIG. 2, an SPR sensor cell 100 is formed in a shape of a bottomed frame having a substantially rectangular shape in a plan view, and includes an under-cladding layer 11, a core layer 12 including a uniform refractive index layer 12a and a graded refractive index layer 2b, a protective layer 13 covering an upper surface of the under-cladding layer 11 and the core layer 12, and a metal layer 14 formed on the protective layer 13 and covering the core layer 12. The under-cladding layer 11, the core layer 12, the protective layer 13, and the metal layer 14 form an optical waveguide, and serve as a detection unit 10 configured to detect a state of a sample and/or a change thereof. In the illustrated embodiment, the SPR sensor cell 100 includes a sample mounting portion 20 formed so as to be adjacent to the detection unit 10. The sample mounting portion 20 is defined by an over-cladding layer 15. The protective layer 13 may be omitted depending on the purpose. The over-cladding layer 15 may also be omitted as long as the sample mounting portion 20 can be formed appropriately. In the sample mounting portion 20, a sample (for example, a solution or powder) to be analyzed is mounted so as to come into contact with the detection unit (substantially, the metal layer).

The under-cladding layer 11 is formed in a shape of a plate having a substantially rectangular shape in a plan view, with a predetermined thickness. The thickness of the under-cladding layer (thickness from an upper surface of the core layer) is, for example, from 5 μm to 400 μm.

The core layer 12 is formed substantially in a square column shape extending in a direction orthogonal to both a width direction (right and left direction of the figure surface of FIG. 2) and a thickness direction of the under-cladding layer 11, and is buried in an upper end portion substantially at the center of the width direction of the under-cladding layer 11. The direction in which the core layer 12 extends serves as a direction in which light is propagated in the optical waveguide.

The core layer 12 is arranged so that the upper surface thereof is flush with an upper surface of the under-cladding layer 11. The metal layer can be arranged efficiently only on an upper side of the core layer by arranging the core layer so that the upper surface thereof is flush with the upper surface of the under-cladding layer. Further, the core layer is arranged so that both end surfaces thereof in the extending direction are flush with both end surfaces of the under-cladding layer in the extending direction.

In the present invention, the core layer 12 includes the uniform refractive index layer 12a and the graded refractive index layer 12b. The graded refractive index layer 12b is arranged on the uniform refractive index layer 12a (in other words, between the uniform refractive index layer 12a and the metal layer 14).

The uniform refractive index layer 12a has a uniform refractive index. The refractive index ($N_{CO}$) of the uniform refractive index layer is preferably 1.43 or less, more preferably less than 1.40, still more preferably 1.38 or less. When the refractive index of the uniform refractive index layer is set to 1.43 or less, the detection sensitivity can be markedly improved. The lower limit of the refractive index of the uniform refractive index layer is preferably 1.34. When the refractive index of the uniform refractive index layer is 1.34 or more, SPR can be excited even in an aqueous solution-based sample (refractive index of water: 1.33), and a generally used material can be used. It should be noted that, as used herein, the refractive index refers to a refractive index at a wavelength of 830 nm. Further, the "uniform refractive index" as used herein includes the case where a variation in refractive index in any plane is less than 0.001.

The refractive index ($N_{CO}$) of the uniform refractive index layer 12a is higher than the refractive index ($N_{CL}$) of the under-cladding layer 11. The difference ($N_{CO}-N_{CL}$) between the refractive index of the uniform refractive index layer and the refractive index of the under-cladding layer is preferably 0.010 or more, more preferably 0.020 or more, still more preferably 0.025 or more. When the difference between the refractive index of the uniform refractive index layer and the refractive index of the under-cladding layer falls within such range, the optical waveguide of the detection unit can be set to a so-called multimode. Thus, the amount of light transmitted through the optical waveguide can be increased, and as a result, the S/N ratio can be enhanced. Further, the difference between the refractive index of the uniform refractive index layer and the refractive index of the under-cladding layer is preferably 0.15 or less, more preferably 0.10 or less, still more preferably 0.050 or less. When the difference between the refractive index of the uniform refractive index layer and the refractive index of the under-cladding layer falls within such range, light at an angle of reflection at which the excitation of SPR occurs can exist in the core layer.

The graded refractive index layer 12b has a refractive index which is equal to or greater than that of the uniform refractive index layer 12a and which increases continuously from a surface thereof on the uniform refractive index layer 12a side to the metal layer 14 side in a thickness direction of the graded refractive index layer 12b. When the graded refractive index layer having such a refractive index change is formed on the metal layer side in the core layer, the SPR sensor cell having increased signal intensity can be obtained. The mechanism under which the above-mentioned effect is exhibited is not exactly known and does not limit the present invention, but is assumed to be as described below. That is, it is assumed that, due to the presence of the graded refractive index layer, the angle of reflection of light propagated in the optical waveguide (core layer) is changed to an angle advantageous to the excitation of SPR, and hence the amount of light reflected at an angle for causing a large SPR signal increases, with the result that SPR is strongly excited to obtain a large SPR signal. In contrast, in the related-art SPR sensor cell disclosed in Patent Literature 2, the graded refractive index layer has a refractive index that decreases continuously toward the under-cladding layer side and is arranged on the under-cladding side in the core layer. Such graded refractive index layer is considered to serve to introduce light into the uniform refractive index layer so that the amount of light in the uniform refractive index layer increases, and thus the action and effect thereof are different from those of the graded refractive index layer of the present invention. It should be noted that it is preferred that the graded refractive index layer 12b have a refractive index that increases continuously from the surface thereof on the uniform refractive index layer 12a side to a surface thereof on the metal layer 14 side in the thickness direction of the graded refractive index layer 12b, but the refractive index of a surface layer portion on the metal layer side may be substantially uniform within a range not impairing the effects of the present invention. The thickness of the surface layer portion having a substantially uniform refractive index is generally 20% or less of the thickness of the graded refractive index layer, for example, 3 μm or less, preferably 2 μm or less, more preferably 1 μm or less.

A minimum refractive index ($N_{min}$) of the graded refractive index layer 12b is generally a refractive index in the surface on the uniform refractive index layer 12a side and is equal to the refractive index of the uniform refractive index layer. It is preferred that a maximum refractive index ($N_{max}$) of the graded refractive index layer be a value satisfying a refractive index change described later, and the maximum refractive index ($N_{max}$) may be, for example, 1.341 or more and 1.465 or less.

A refractive index change ($\Delta N = N_{max} - N_{min}$) in the graded refractive index layer 12b is preferably 0.001 or more, more preferably 0.005 or more, still more preferably 0.010 or more. When the refractive index change is 0.001 or more, the angle of reflection of light propagated in the optical waveguide can be changed to an angle advantageous to the excitation of SPR. The upper limit value of the refractive index change is not particularly limited and can be set to 0.035 from the viewpoint of ease of production.

A change ratio (refractive index change ($\Delta N$)/thickness (Tb)) of the refractive index in the thickness direction when the thickness of the graded refractive index layer 12b is defined as Tb (μm) is preferably from $0.5 \times 10^{-3}$ to $20.0 \times 10^{-3}$, more preferably from $0.8 \times 10^{-3}$ to $16.0 \times 10^{-3}$, still more preferably from $1.0 \times 10^{-3}$ to $15.0 \times 10^{-3}$. In the case where the change ratio ($\Delta N/Tb$) of the refractive index in the thickness direction falls within such a range, the angle of reflection of light propagated in the optical waveguide can be suitably changed to an angle advantageous to the excitation of SPR.

The thickness (Tb) of the graded refractive index layer 12b is preferably from 1 μm to 30 μm, more preferably from 2 μm to 25 μm, still more preferably from 3 μm to 20 μm. When the thickness of the graded refractive index layer is set to be relatively small as described above, the angle of reflection of light propagated in the optical waveguide can be suitably changed to an angle advantageous to the excitation of SPR. On the other hand, it is preferred that a thickness (Ta) of the uniform refractive index layer 12a be equal to or greater than the thickness (Tb) of the graded refractive index layer from the viewpoint of enlarging a core diameter so as to cause a sufficient amount of light to enter the optical waveguide. Specifically, Ta and Tb satisfy preferably a relationship of $1 \leq Ta/Tb$, more preferably a relationship of $1.5 \leq Ta/Tb$, still more preferably a relationship of $3 \leq Ta/Tb \leq 50$. The thickness (Ta) of the uniform refractive index layer may be, for example, from 4 μm to 199 μm. It should be noted that the thickness of the core layer 12 (total thickness of the uniform refractive index layer and the graded refractive index layer) is, for example, from 5 μm to 200 μm, preferably from 20 μm to 200 μm. Further, the width of the core layer is, for example, from 5 μm to 200 μm, preferably from 20 μm to 200 μm. With such thickness and/or width, the optical waveguide can be set to a so-called multimode.

As a material for forming the uniform refractive index layer 12a, any suitable material can be used as long as the effects of the present invention are obtained. Specific examples thereof include a fluorine resin, an epoxy resin, a polyimide resin, a polyamide resin, a silicone resin, an acrylic resin, and modified products thereof (for example, a fluorene-modified product, a deuterium-modified product, and a fluorine-modified product in the case of the resins other than the fluorine resin). Those resins may be used alone or in combination. Those resins can each be used as a photosensitive material preferably by being blended with a photosensitizing agent. The under-cladding layer 11 can be formed of a material that is similar to that for forming the uniform refractive index layer and is adjusted so that the refractive index thereof becomes lower than that of the uniform refractive index layer.

The graded refractive index layer 12b may be formed through use of any suitable material as long as the above-mentioned refractive index is obtained. For example, the graded refractive index layer may be formed by causing a material having a refractive index higher than that of a uniform refractive index layer formed in advance to permeate the surface of the uniform refractive index layer on the metal layer side so that a composition gradient is formed (that is, the composition changes continuously) in the thickness direction of the graded refractive index layer, and fixing the gradient. Further, for example, the graded refractive index layer may be formed by causing a cross-linking density gradient to be formed in the thickness direction of the graded refractive index layer through use of the same material as that for forming the uniform refractive index layer.

As the material that is caused to permeate the uniform refractive index layer, any suitable material is used as long as the material has a refractive index higher than that of the uniform refractive index layer and may permeate the uniform refractive index layer so as to form a composition gradient to be cured. A material having a refractive index from 1.400 to 1.600 is preferred. A specific example of such material includes a polymerizable monomer such as (meth)acrylic monomer having a refractive index from 1.400 to 1.600.

The protective layer 13 is formed as a thin-film having the same shape as that of the under-cladding layer 11 in a plan view so as to cover the entire upper surfaces of the under-cladding layer 11 and the core layer 12, as necessary. Unlike the illustrated example, the protective layer may be formed so as to cover a part of the upper surfaces of the under-cladding layer and the core layer. When the protective layer is formed, for example, in the case where a sample is in a liquid form, the core layer and/or the cladding layer can be prevented from becoming swollen with the sample. As the material for forming the protective layer, for example, there may be given silicon dioxide and aluminum oxide. These materials may be preferably adjusted so that the refractive index becomes lower than that of the core layer. The thickness of the protective layer is preferably from 1 nm to 100 nm, more preferably from 5 nm to 20 nm.

As illustrated in FIG. 2, the metal layer 14 is formed so as to uniformly cover the upper surface of the core layer 12 through intermediation of the protective layer 13. In this case, as necessary, an easy-adhesion layer (not shown) may be formed between the protective layer 13 and the metal layer 14. When the easy-adhesion layer is formed, the protective layer and the metal layer can be fixed to each other firmly. Instead of forming the protective layer, the metal layer may directly cover the core layer.

As a material for forming the metal layer 14, there may be given gold, silver, platinum, copper, aluminum, and alloys thereof. The metal layer may be a single layer or may have a laminate structure of two or more layers. The thickness (total thickness of all the layers in the case of the laminate structure) of the metal layer is preferably from 20 nm to 70 nm, more preferably from 30 nm to 60 nm.

As a material for forming the easy-adhesion layer, there may be typically given chromium or titanium. The thickness of the easy-adhesion layer is preferably from 1 nm to 5 nm.

As illustrated in FIG. 1, the over-cladding layer 15 is formed in the shape of a frame having a rectangular shape in a plan view so that an outer circumference of the over-cladding layer 15 becomes substantially flush with an outer circumference of the under-cladding layer 11 in a plan view, on the upper surfaces of the under-cladding layer 11 and the core layer 12 (upper surface of the protective layer 13 in the illustrated example). A portion surrounded by the upper surfaces of the under-cladding layer 11 and the core layer 12 (upper surface of the protective layer 13 in the illustrated example) and the over-cladding layer 15 is partitioned as the sample mounting portion 20. When a sample is mounted in the partitioned portion, the metal layer of the detection unit 10 and the sample come into contact with each other so that detection can be performed. Further, through the formation of such partitioned portion, a sample can be easily mounted on the surface of the metal layer, and hence the operability can be enhanced.

As a material for forming the over-cladding layer 15, for example, there may be given the materials for forming the core layer and the under-cladding layer, and silicone rubber. The thickness of the over-cladding layer is preferably from 5 μm to 2,000 μm, more preferably from 25 μm to 200 μm. The refractive index of the over-cladding layer is preferably lower than the refractive index of the core layer. In one embodiment, the refractive index of the over-cladding layer is equal to the refractive index of the under-cladding layer. It should be noted that, in the case where the protective layer having a refractive index lower than that of the core layer is formed, the refractive index of the over-cladding layer may not be necessarily required to be lower than that of the refractive index of the core layer.

Although the SPR sensor cell according to the preferred embodiment of the present invention has been described, the present invention is not limited thereto. For example, in the relationship between the core layer and the under-cladding layer, the core layer only needs to be formed so that at least a part thereof is adjacent to the under-cladding layer. For example, although a configuration in which the core layer is buried in the under-cladding layer is described in the above-mentioned embodiment, the core layer may be formed so as to pass through the under-cladding layer. Besides, the core layer may be formed on the under-cladding layer so that a predetermined portion of the core layer is surrounded by the over-cladding layer.

Further, the number of core layers in the SPR sensor may be changed depending on the purpose. Specifically, a plurality of the core layers may be formed at a predetermined interval in the width direction of the under-cladding layer. With such a configuration, a plurality of samples can be analyzed simultaneously, and hence analysis efficiency can be enhanced. As the shape of the core layer, any suitable shape (for example, a semicircular column shape or a convex column shape) can be adopted depending on the purpose.

Figure 3:
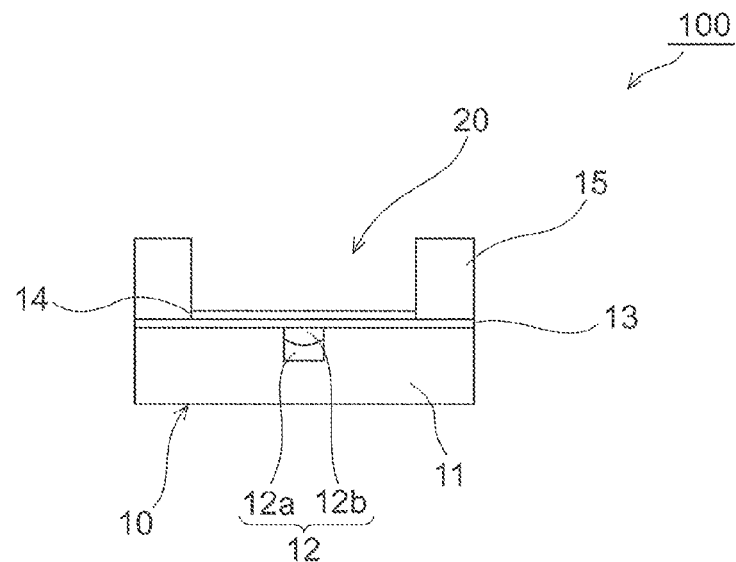
FIG. 3 is a schematic sectional view of an SPR sensor cell according to another preferred embodiment of the present invention.

Further, each of the uniform refractive index layer and the graded refractive index layer is not required to have a strictly uniform thickness and may have a non-uniform thickness, for example, as illustrated in FIG. 3. In this case, as the thickness of the uniform refractive index layer and the graded refractive index layer, the maximum thickness in each layer is adopted.

Further, a lid may be provided on an upper portion of the SPR sensor cell 100 (sample mounting portion 20). With such a configuration, a sample can be prevented from coming into contact with ambient air. In addition, in the case where the sample is a solution, a change in concentration caused by evaporation of a solvent can be prevented. In the case of providing a lid, an injection port for injecting a liquid sample into the sample mounting portion and a discharge port for discharging the liquid sample from the sample mounting portion may be formed. With such a configuration, the sample can be allowed to flow to be supplied to the sample mounting portion continuously, and hence the characteristics of the sample can be measured continuously.

The above-mentioned embodiments may be combined appropriately.

B. Method of Producing SPR Sensor Cell

The SPR sensor cell of the present invention may be produced by any suitable method. Now, an example of the method of producing an SPR sensor cell of the present invention is described with reference to FIGS. 4A-4G.

Figure 4A:
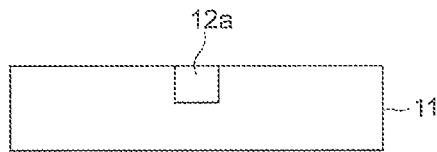
FIGS. 4A-4G are schematic sectional views for illustrating an example of a method of producing an SPR sensor cell of the present invention.

First, an optical waveguide film having a core layer (uniform refractive index layer 12a) buried in the under-cladding layer 11 as illustrated in FIG. 4A is produced by any suitable method. As a specific example of the method of producing the optical waveguide film, there are given a method illustrated in FIGS. 5A-5G and a method illustrated in FIG. 3 of Japanese Patent Application Laid-open No. 2012-215541.

Figure 5A:
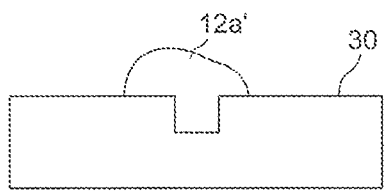
FIGS. 5A-5G are schematic sectional views for illustrating an example of a method of producing an optical waveguide film to be used in the SPR sensor cell of the present invention.
Figure 5B:
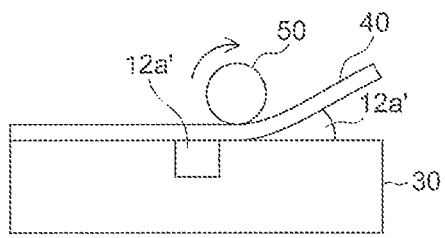
Figure 5C:
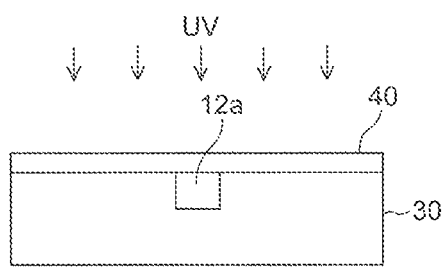
Figure 5D:
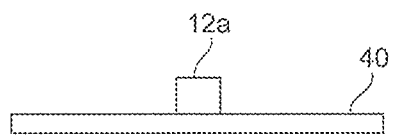
Figure 5E:
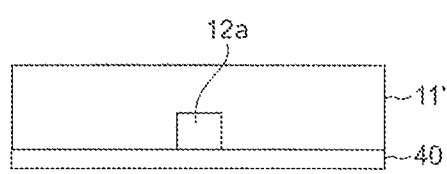
Figure 5F:
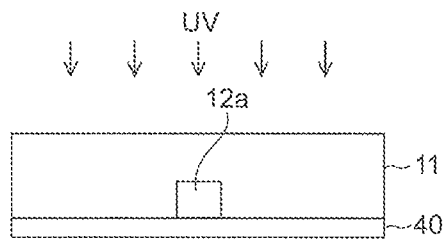
Figure 5G:
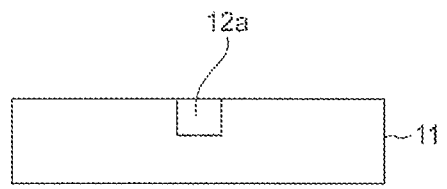

In the method illustrated in FIGS. 5A-5G, first, as illustrated in FIG. 5A, a material 12a' for forming a uniform refractive index layer is applied to a surface of a die 30 having a recessed portion corresponding to the shape of the core layer. Then, as illustrated in FIG. 5B, a transfer film 40 is bonded onto the surface of the die 30 while the transfer film 40 is pressed with pressing means 50 in a predetermined direction, and thus the excessive material 12a' for forming a uniform refractive index layer is removed while the material 12a' for forming a uniform refractive index layer is filled into the recessed portion. Then, as illustrated in FIG. 5C, the material 12a' for forming a uniform refractive index layer filled into the recessed portion is irradiated with ultraviolet rays to cure the material, to thereby form the uniform refractive index layer 12a. The irradiation conditions of ultraviolet rays may be set appropriately depending on the type of the material for forming a uniform refractive index layer. The material for forming a uniform refractive index layer may be heated as necessary. The heating may be performed before or after the irradiation with ultraviolet rays, or simultaneously with the irradiation with ultraviolet rays. The heating conditions may be set appropriately depending on the type of the material for forming a uniform refractive index layer. Then, as illustrated in FIG. 5D, the transfer film 40 is peeled from the die 30, and thus the uniform refractive index layer 12a is transferred onto the transfer film 40. Then, as illustrated in FIG. 5E, a material 11' for forming an under-cladding layer is applied so as to cover the uniform refractive index layer 12a. After that, as illustrated in FIG. 5F, the material 11' for forming an under-cladding layer is irradiated with ultraviolet rays to cure the material, to thereby form the under-cladding layer 11. The irradiation conditions of ultraviolet rays may be set appropriately depending on the type of the material for forming an under-cladding layer. Then, as illustrated in FIG. 5G, the transfer film 40 is removed by peeling and inverted, to thereby obtain an optical waveguide film having the uniform refractive index layer 12a buried in the under-cladding layer 11.

Figure 4B:
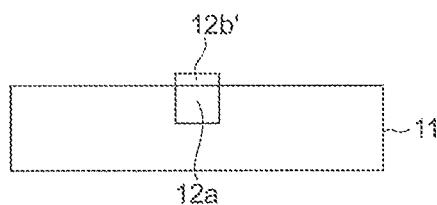
Figure 4C:
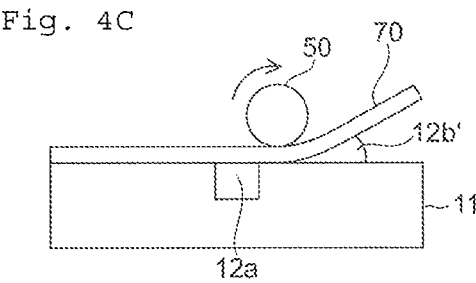

Then, as illustrated in FIG. 4B, a material 12b' having a refractive index higher than that of the uniform refractive index layer is applied to an upper surface (exposed surface) of the uniform refractive index layer 12a of the above-mentioned optical waveguide film. The applied high refractive index material 12b' permeates the surface of the uniform refractive index layer 12a, and thus a composition gradient (as a result, a refractive index gradient) may be formed in the thickness direction of the uniform refractive index layer 12a. Immediately after the high refractive index material 12b' is applied or after the high refractive index material 12b' is left as is for a predetermined period of time, as illustrated in FIG. 4C[[at (c)]], a release film 70 is bonded onto an upper surface of the under-cladding layer 11 while the release film 70 is pressed with the pressing means 50 in a predetermined direction, to thereby remove the excessive high refractive index material 12b'. Although the ease of permeation of the high refractive index material is varied depending on the type thereof, the permeation amount generally tends to be increased by extending a period of time from the application of the high refractive index material to the removal thereof (hereinafter referred to as "permeation time"). Thus, the thickness of the uniform refractive index layer and the graded refractive index layer can be adjusted by controlling the permeation time. The permeation time is, for example, from 5 seconds to 120 minutes, preferably from 10 seconds to 60 minutes. It should be noted that, as necessary, the high refractive index material 12b' may be caused to permeate the uniform refractive index layer 12a with heating. The heating temperature is, for example, from 40° C. to 100° C.

Figure 4D:
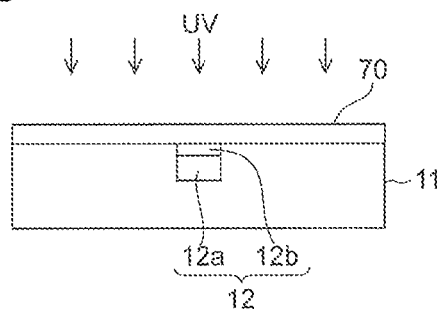

Next, as illustrated in FIG. 4D, irradiated with ultraviolet rays from the release film 70 side cures the high refractive index material 12b', to thereby form the graded refractive index layer 12b (specifically, in the uniform refractive index layer 12a, a region which the high refractive index material 12b' has permeated serves as the graded refractive index layer 12b). In this case, it is preferred that the high refractive index material having permeated the uniform refractive index layer 12a be cured immediately after the removal of the excessive high refractive index material. This is because the refractive index gradient can be prevented from being disturbed. The irradiation conditions of ultraviolet rays may be appropriately set depending on the type of the high refractive index material.

Figure 4E:
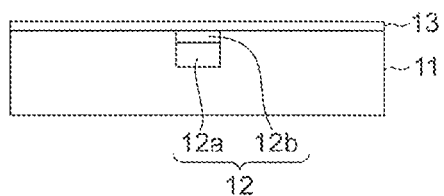

Then, the release film 70 is removed by peeling, and as necessary, the protective layer 13 is formed on the under-cladding layer 11 and the core layer 12, as illustrated in FIG. 4E. The protective layer is formed, for example, by subjecting a material for forming a protective layer to sputtering or vapor deposition. In the case of forming the protective layer, an easy-adhesion layer (not shown) is preferably formed on the protective layer. The easy-adhesion layer is formed, for example, by subjecting chromium or titanium to sputtering.

Figure 4F:
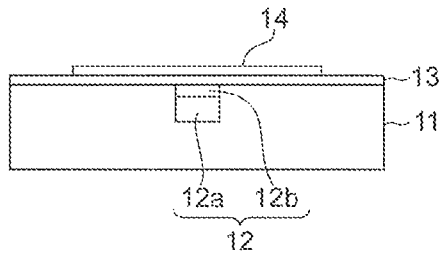

Next, as illustrated in FIG. 4F, the metal layer 14 is formed on the protective layer 13 (upper surfaces of the core layer and the under-cladding layer in the case where the protective layer is not formed) so as to cover the core layer 12. Specifically, the metal layer 14 is formed, for example, by subjecting a material for forming a metal layer to vacuum deposition, ion plating, or sputtering through a mask having a predetermined pattern.

Figure 4G:
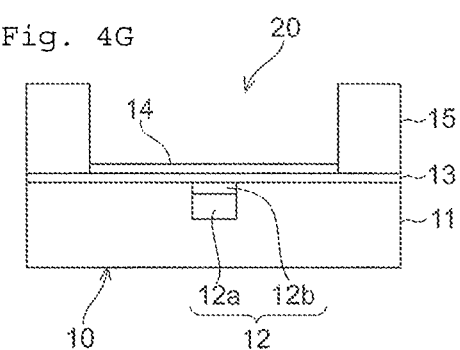

Finally, as illustrated in FIG. 4G, the over-cladding layer 15 having the predetermined frame shape is formed. The over-cladding layer 15 may be formed by any suitable method. The over-cladding layer 15 may be formed, for example, by arranging a die having the predetermined frame shape on the protective layer 13, filling the die with varnish of a material for forming an over-cladding layer, drying the varnish, curing the varnish as necessary, and finally removing the die. In the case of using a photosensitive material, the over-cladding layer 15 may be formed by applying the varnish over the entire surface of the protective layer 13, drying the varnish, and then exposing the varnish to light through a photomask having a predetermined pattern, followed by development.

As described above, the SPR sensor cell of FIG. 1 can be produced.

C. SPR Sensor

Figure 6:
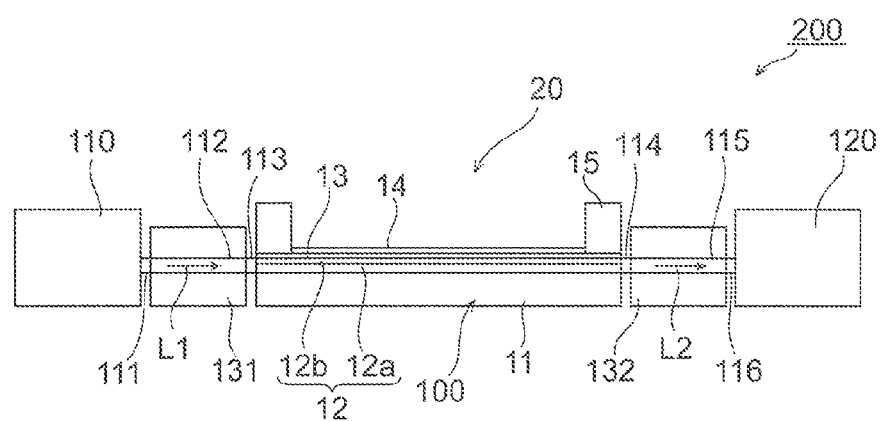
FIG. 6 is a schematic sectional view for illustrating an SPR sensor according to a preferred embodiment of the present invention.

FIG. 6 is a schematic sectional view for illustrating an SPR sensor according to a preferred embodiment of the present invention. An SPR sensor 200 includes the SPR sensor cell 100, a light source 110, and an optical measuring instrument 120. The SPR sensor cell 100 is the SPR sensor of the present invention described in the above-mentioned sections A and B.

As the light source 110, any suitable light source may be adopted. Specific examples of the light source include a white light source and a monochromatic light source. The optical measuring instrument 120 is connected to any suitable arithmetic processing device, and enables accumulation, display, and processing of data.

The light source 110 is connected to a light source side optical fiber 112 through a light source side optical connector 111. The light source side optical fiber 112 is connected to one side end portion of the SPR sensor cell 100 (core layer 12) in a propagation direction through a light source side fiber block 113. A measuring instrument side optical fiber 115 is connected to the other side end portion of the SPR sensor cell 100 (core layer 12) in the propagation direction through a measuring instrument side fiber block 114. The measuring instrument side optical fiber 115 is connected to the optical measuring instrument 120 through a measuring instrument side optical connector 116. It is preferred that the connection be performed through use of a multimode optical fiber, which can propagate light at an angle of reflection capable of exciting SPR in the optical waveguide.

The SPR sensor cell 100 is fixed by any suitable sensor cell fixing device (not shown). The sensor cell fixing device is movable in a predetermined direction (for example, a width direction of the SPR sensor cell), and thus the SPR sensor cell can be arranged at a desired position.

The light source side optical fiber 112 is fixed by a light source side optical fiber fixing device 131, and the measuring instrument side optical fiber 115 is fixed by a measuring instrument side optical fiber fixing device 132. The light source side optical fiber fixing device 131 and the measuring instrument side optical fiber fixing device 132 are each fixed to any suitable six-axis movable stage (not shown) so as to be movable in the propagation direction of the optical fiber, width direction (direction orthogonal to the propagation direction in a horizontal direction) and thickness direction (direction orthogonal to the propagation direction in a perpendicular direction), and rotatable about axes in the above-mentioned respective directions.

In the SPR sensor as described above, the light source 110, the light source side optical fiber 112, the SPR sensor cell 100 (core layer 12), the measuring instrument side optical fiber 115, and the optical measuring instrument 120 can be arranged on one axis, and light can be guided from the light source 110 so as to be transmitted therethrough.

An example of the manner of use of such SPR sensor is described below.

First, a sample is mounted on the sample mounting portion 20 of the SPR sensor cell 100 so that the sample and the metal layer 14 are brought into contact with each other. Then, predetermined light from the light source 110 is guided to the SPR sensor cell 100 (core layer 12) through the light source side optical fiber 112 (see the arrow L1 of FIG. 6). The light guided to the SPR sensor cell 100 (core layer 12) is transmitted through the SPR sensor cell 100 (core layer 12) while repeating total reflection in the core layer 12 with an angle of reflection varied by the graded refractive index layer 12b, and part of the light enters the metal layer 14 on an upper surface of the core layer 12 and is attenuated by surface plasmon resonance. The light transmitted through the SPR sensor cell 100 (core layer 12) is guided to the optical measuring instrument 120 through the measuring instrument side optical fiber 115 (see the arrow L2 of FIG. 6). That is, in the SPR sensor 200, the intensity of light having a wavelength generating surface plasmon resonance in the core layer is attenuated in the light guided to the optical measuring instrument 120. The wavelength of light generating surface plasmon resonance depends on, for example, the refractive index of the sample brought into contact with the metal layer 14. Therefore, through the detection of the attenuation of the light intensity of the light guided to the optical measuring instrument 120, a change in refractive index of the sample can be detected.

For example, in the case of using a white light source as the light source 110, a change in refractive index of the sample can be confirmed by measuring the wavelength of light whose light intensity is attenuated after the transmission through the SPR sensor cell 100 (wavelength of light generating surface plasmon resonance) with the optical measuring instrument 120 and detecting a change in wavelength of the light whose light intensity is attenuated. In addition, for example, in the case of using a monochromatic light source as the light source 110, a change in wavelength of light generating surface plasmon resonance can be confirmed and a change in refractive index of the sample can be confirmed by measuring a change (attenuation degree) in light intensity of monochromatic light after the transmission through the SPR sensor cell 100 with the optical measuring instrument 120 and detecting a change in attenuation degree.

As described above, such an SPR sensor cell can be used, for example, for various chemical analyses and biochemical analyses such as the measurement of a sample concentration and the detection of an immunoreaction, based on a change in refractive index of the sample. More specifically, for example, in the case where the sample is a solution, the refractive index of the sample (solution) depends on the concentration of the solution, and hence the concentration of the sample can be measured by detecting the refractive index of the sample. Further, a change in concentration of the sample can be confirmed by detecting a change in refractive index of the sample. In addition, for example, in the detection of an immunoreaction, an antibody is fixed onto the metal layer 14 of the SPR sensor cell 100 through intermediation of a dielectric film, and an analyte is brought into contact with the antibody. If the antibody and the analyte perform an immunoreaction, the refractive index of the sample changes. Therefore, it can be determined that the antibody and the analyte have performed an immunoreaction by detecting a change in refractive index of the sample before and after the contact between the antibody and the analyte.

EXAMPLES

The present invention is hereinafter described specifically by way of Examples. However, the present invention is not limited to the Examples below. It should be noted that, unless otherwise specified, a measurement wavelength for a refractive index is 830 nm in the Examples and Comparative Examples.

<Measurement of Refractive Index>

The refractive index was measured by forming a film having a thickness of 10 μm on a silicon wafer and measuring the refractive index of the film at a wavelength of 830 nm through use of a prism coupler refractive index measurement device.

<Measurement of Change in Refractive Index Having Gradient>

The change in refractive index having a gradient was measured through use of a refractive index distribution measurement device manufactured by Mizojiri Optical Co., Ltd. Specifically, a measurement sample (thickness: about 50 μm, width: 200 mm) cut with a dicer (manufactured by DISCO Corporation) so that the length of an optical waveguide became 100 μm was placed on a slide glass, and the cross-section thereof was measured. In order to reduce a measurement error caused by surface roughness of the cut cross-section, pure water was dropped onto the sample and a cover glass was placed on the sample so that the surface of the sample became smooth, and thus interference fringes were measured. The analysis resolution of measuring a refractive index was 0.214×0.214 μm. A refractive index distribution of a measurement region can be determined based on a shift amount of the interference fringes of light thus measured.

<Measurement of Thickness of Graded Refractive Index Layer>

The light intensity distribution in the core layer was measured through use of a beam pattern measurement system (M-Scope type L manufactured by Synergy Optosystems Co., Ltd.). Specifically, light from a halogen light source ("HL-2000-HP" trade name) manufactured by Ocean Optics, Inc., white light) was introduced into an incident-side end surface of the core layer of the SPR sensor cell through a graded multimode fiber (Φ50 μm), and the light intensity distribution in the core layer was measured with the beam pattern measurement system connected to an output side of the core layer. Then, the thickness of the graded refractive index layer was calculated based on the measurement value of the light intensity distribution.

Example 1

An optical waveguide film having a core layer (uniform refractive index layer) buried in an under-cladding layer was produced by a method illustrated in FIGS. 5A-5G. Specifically, a material for forming a uniform refractive index layer was dropped onto a surface of a die (length: 200 mm, width: 200 mm) in which a recessed portion for forming a core layer having a width of 50 μm and a length (depth) of 50 μm was formed on its surface. One end of a corona-treated surface of a polypropylene (PP) film (thickness: 40 μm) having one surface subjected to corona treatment was brought into abutment against the surface of the die, and the other end was allowed to be warped. In this state, a roller was rotated toward the other end side while pressing the abutment part between the die and the PP film from the PP film side to thereby bond the die and the PP film to each other. With this, the material for forming a uniform refractive index layer was filled into the recessed portion of the die, and the excessive material for forming a uniform refractive index layer was pushed out. Then, the laminate thus obtained was irradiated with ultraviolet rays from the PP film side to cure the material for forming a uniform refractive index layer completely, to thereby form a uniform refractive index layer (refractive index: 1.384). It should be noted that the material for forming a uniform refractive index layer was prepared by stirring and dissolving 60 parts by weight of a fluorine-based UV-curable resin ("OP38Z" (trade name) manufactured by DIC Corporation) and 40 parts by weight of a fluorine-based UV-curable resin ("OP40Z" (trade name) manufactured by DIC Corporation). Then, the PP film was peeled from the die to transfer the uniform refractive index layer having a substantially square column shape with a thickness of 50 μm and a width of 50 μm onto the film.

A material for forming an under-cladding layer (fluorine-based UV-curable resin ("Fluorolink MD700" (trade name) manufactured by Solvay Specialty Polymers Japan K. K.)) was applied to the PP film so as to cover the uniform refractive index layer. At this time, the material for forming an under-cladding layer was applied so that the thickness from a surface (upper surface) of the uniform refractive index layer became 100 μm. Then, the resultant was irradiated with ultraviolet rays to cure the material for forming an under-cladding layer, to thereby form an under-cladding layer (refractive index: 1.347). Then, the PP film was removed by peeling and the under-cladding layer and the core layer (uniform refractive index layer) were inverted. As described above, an optical waveguide film having a core layer (uniform refractive index layer) buried in an under-cladding layer was produced.

Then, an SPR sensor cell was produced by a method similar to the method illustrated in FIGS. 4A-4G. Specifically, n-butyl acrylate (refractive index: 1.456) was applied as a high refractive index material to an exposed surface of the core layer (uniform refractive index layer) of the above-mentioned optical waveguide film. Immediately after the application, one end of a release-treated surface of a PET film (thickness: 45 μm) subjected to release treatment was brought into abutment against an upper surface of the optical waveguide film, and the other end was allowed to be warped. In this state, a roller was rotated toward the other end side while pressing the abutment part from the PET film side to thereby bond the optical waveguide film and the PET film to each other. With this, the high refractive index material was caused to permeate the core layer (uniform refractive index layer) to push out the excessive high refractive index material (permeation time: about 5 seconds). Then, the laminate thus obtained was irradiated with ultraviolet rays from the PET film side to cure the high refractive index material to thereby form a graded refractive index layer. Then, the PET film was removed by peeling.

Then, the optical waveguide film was cut by dicing to a length of 22.25 mm and a width of 20 mm, and thereafter, gold was sputtered so as to cover the core layer through a mask having an opening with a length of 6 mm and a width of 1 mm, to thereby form a metal layer (thickness: 30 nm). Finally, an over-cladding layer having a frame shape was formed through use of the same material as that for forming an under-cladding layer by a method similar to that of forming the under-cladding layer. Thus, an SPR sensor cell, which was the same as the SPR sensor cell illustrated in FIG. 1 and FIG. 2 aside from not having the protective layer, was produced.

The SPR sensor cell obtained as described above, a halogen light source ("HL-2000-HP" (trade name) manufactured by Ocean Optics, Inc., white light), and a spectroscope ("USB4000" (trade name) manufactured by Ocean Optics, Inc.) were arranged on one axis and connected to each other to produce an SPR sensor as illustrated in FIG. 6. Specifically, the halogen light source ("HL-2000-HP" (trade name) manufactured by Ocean Optics, Inc., white light) was connected to an incident side of the SPR sensor cell (core layer) through a graded multimode fiber (Φ50 μm/125 μm) so that light from the light source was introduced into an incident-side end surface of the core layer of the SPR sensor cell, and the spectroscope ("USB4000" (trade name) manufactured by Ocean Optics, Inc.) was connected to an output side of the core layer of the SPR sensor cell. Then, 40 μL of pure water (refractive index: 1.330) or 10 vol % ethylene glycol aqueous solution (refractive index: 1.3436) was loaded as a sample into a sample mounting portion of the SPR sensor cell and subjected to measurement. Further, a transmittance spectrum of each sample was determined in the case where light intensity at each wavelength when light was transmitted through the SPR sensor cell (optical waveguide) under the condition that the sample was not mounted was set to 100%, and peak intensity at a time of measurement of pure water and a peak intensity change amount at a particular wavelength at which the largest difference was caused in transmittance intensity between the time of measurement of pure water and the time of measurement of the ethylene glycol aqueous solution were measured. In this case, the large peak intensity means that the SPR peak intensity is large, and a larger peak intensity change indicates higher detection sensitivity. The results are shown in Table 1.

Example 2

An SPR sensor cell and an SPR sensor were produced in the same way as in Example 1 except that 2,2,2-trifluoro-ethyl methacrylate (refractive index: 1.411) was used as the high refractive index material. The SPR sensor thus obtained was subjected to the same evaluation as that of Example 1. The results are shown in Table 1.

Example 3

An SPR sensor cell and an SPR sensor were produced in the same way as in Example 1 except that 2-phenoxyethyl methacrylate (refractive index: 1.512) was used as the high refractive index material. The SPR sensor thus obtained was subjected to the same evaluation as that of Example 1. The results are shown in Table 1.

Example 4

An SPR sensor cell and an SPR sensor were produced in the same way as in Example 1 except that 2,2,2-trifluoro-ethyl methacrylate (refractive index: 1.411) was used as the high refractive index material and that the permeation time was set to 3 minutes. The SPR sensor thus obtained was subjected to the same evaluation as that of Example 1. The results are shown in Table 1.

Example 5

An SPR sensor cell and an SPR sensor were produced in the same way as in Example 1 except that 2-phenoxyethyl methacrylate (refractive index: 1.512) was used as the high refractive index material and that the permeation time was set to 3 minutes. The SPR sensor thus obtained was subjected to the same evaluation as that of Example 1. The results are shown in Table 1.

Example 6

An SPR sensor cell and an SPR sensor were produced in the same way as in Example 1 except that the permeation time was set to 3 minutes. The SPR sensor thus obtained was subjected to the same evaluation as that of Example 1. The results are shown in Table 1.

Example 7

An SPR sensor cell and an SPR sensor were produced in the same way as in Example 1 except that the permeation time was set to 5 minutes. The SPR sensor thus obtained was subjected to the same evaluation as that of Example 1. The results are shown in Table 1.

Example 8

An SPR sensor cell and an SPR sensor were produced in the same way as in Example 1 except that the permeation time was set to 10 minutes. The SPR sensor thus obtained was subjected to the same evaluation as that of Example 1. The results are shown in Table 1.

Comparative Example 1

An SPR sensor cell and an SPR sensor were produced in the same way as in Example 1 except that the application, removal, and curing with ultraviolet rays of the high refractive index material were not performed (as a result, the graded refractive index layer was not formed). The SPR sensor thus obtained was subjected to the same evaluation of Example 1. The results are shown in Table 1.

TABLE 1

| | Thickness of graded refractive index layer (Tb: μm) | Change in refractive index (ΔN) | Change ratio of refractive index (ΔN/Tb) | Peak intensity at time of measurement of pure water (T %) | Peak intensity change (T %) |
|---|---|---|---|---|---|
| Example 1 | 2 | 0.002 | $1.0 \times 10^{-3}$ | 45 | 22 |
| Example 2 | 2 | 0.014 | $7.0 \times 10^{-3}$ | 50 | 27 |
| Example 3 | 2 | 0.032 | $16.0 \times 10^{-3}$ | 41 | 21 |
| Example 4 | 5 | 0.014 | $2.8 \times 10^{-3}$ | 88 | 39 |
| Example 5 | 5 | 0.021 | $4.2 \times 10^{-3}$ | 63 | 32 |
| Example 6 | 10 | 0.016 | $1.6 \times 10^{-3}$ | 72 | 37 |
| Example 7 | 20 | 0.018 | $0.9 \times 10^{-3}$ | 60 | 35 |
| Example 8 | 30 | 0.018 | $0.6 \times 10^{-3}$ | 40 | 22 |
| Comparative Example 1 | — | — | — | 38 | 20 |

<Evaluation>

As is apparent from Table 1, it is understood that the SPR sensor cells of the Examples have a peak intensity change larger than that of the SPR sensor cell of the comparative example and are excellent in sensitivity.

INDUSTRIAL APPLICABILITY

The SPR sensor cell and the SPR sensor of the present invention can be used suitably in various chemical analyses and biochemical analyses such as the measurement of a sample concentration and the detection of an immunoreaction.

REFERENCE CHARACTER LIST 10 detection unit
11 under-cladding layer
12 core layer
12a uniform refractive index layer
12b graded refractive index layer
13 protective layer
14 metal layer
15 over-cladding layer
20 sample mounting portion
100 SPR sensor cell
110 light source
120 optical measuring instrument
200 SPR sensor

The invention claimed is:

1. SPR sensor cell, comprising:
   an under-cladding layer;
   a core layer formed so that at least a part of the core layer is adjacent to the under-cladding layer; and
   a metal layer covering the core layer,
   wherein the core layer includes a uniform refractive index layer and a graded refractive index layer,
   wherein the graded refractive index layer is arranged between the uniform refractive index layer and the metal layer, and
   wherein a refractive index of the graded refractive index layer is equal to or greater than a refractive index of the uniform refractive index layer, and the refractive index of the graded refractive index layer increases continuously from a surface thereof on a uniform refractive index layer side to a metal layer side in a thickness direction of the graded refractive index layer.

2. The SPR sensor cell according to claim 1, wherein the graded refractive index layer has a thickness from 1 μm to 30 μm.

3. The SPR sensor cell according to claim 1, wherein a change in refractive index (ΔN) of the graded refractive index layer is from 0.001 to 0.035, where ΔN=Nmax−Nmin, Nmax represents a maximum refractive index of the graded refractive index layer, and Nmin represents a minimum refractive index of the graded refractive index layer.

4. The SPR sensor cell according to claim 1, wherein a thickness (Tb (μm)) of the graded refractive index layer and a change in refractive index (ΔN) of the graded refractive index layer satisfy a relationship of $0.5 \times 10^{-3} \leq \Delta N/Tb \leq 20.0 \times 10^{-3}$, where ΔN=Nmax−Nmin, Nmax represents a maximum refractive index of the graded refractive index layer, and Nmin represents a minimum refractive index of the graded refractive index layer.

5. The SPR sensor cell according to claim 1, wherein a refractive index (NCO) of the uniform refractive index layer satisfies a relationship of 1.34≤NCO≤1.43.

6. An SPR sensor, comprising the SPR sensor cell of claim 1.

* * * * *